United States Patent
Pyhälahti et al.

(10) Patent No.: US 11,535,577 B2
(45) Date of Patent: Dec. 27, 2022

(54) OLEFIN TRIMERIZATION

(71) Applicant: Neste Oyj, Espoo (FI)

(72) Inventors: Antti Pyhälahti, Porvoo (FI); Jaana Kanervo, Porvoo (FI)

(73) Assignee: NESTE OYJ, Espoo (FI)

(*) Notice: Subject to any disclaimer, the term of this patent is extended or adjusted under 35 U.S.C. 154(b) by 0 days.

(21) Appl. No.: 17/524,800

(22) Filed: Nov. 12, 2021

(65) Prior Publication Data

US 2022/0144723 A1    May 12, 2022

(30) Foreign Application Priority Data

Nov. 12, 2020 (FI) ........................ 20206143

(51) Int. Cl.
    *C07C 2/28* (2006.01)

(52) U.S. Cl.
    CPC ............ *C07C 2/28* (2013.01); *C07C 2531/08* (2013.01)

(58) Field of Classification Search
    CPC .............................. C07C 2/28; C07C 2531/08
    See application file for complete search history.

(56) References Cited

U.S. PATENT DOCUMENTS

| | | | |
|---|---|---|---|
| 4,544,791 A | 10/1985 | Juguin et al. | |
| 6,613,108 B1* | 9/2003 | Aittamaa | C07C 9/21 585/521 |
| 2005/0137435 A1* | 6/2005 | Tiitta | C07C 5/2518 585/329 |
| 2015/0344383 A1* | 12/2015 | Subramani | C07C 29/04 585/510 |

FOREIGN PATENT DOCUMENTS

| | | |
|---|---|---|
| EP | 1948578 B1 | 6/2011 |
| EP | 2949636 A1 | 12/2015 |
| EP | 2649161 B1 | 5/2018 |
| WO | 2007091862 A1 | 8/2007 |

OTHER PUBLICATIONS

Finnish Office Action dated Mar. 2, 2021 issued in corresponding Finnish Patent Application No. 20206143 by the Finnish Patent and Registration Office. (1 page).
O'Connor, C.T., et al., "The Oligomerization of C4 Alkenes over Cationic Exchange Resins", Applied Catalysis, 1985, pp. 193-207, vol. 16, Elsevier Science Publishers B.V., Amsterdam, The Netherlands. (8 pages).
The extended European Search Report dated Apr. 12, 2022, by the European Patent Office in corresponding European Application No. 21206877.9 (7 pages).

* cited by examiner

*Primary Examiner* — Ali Z Fadhel
(74) *Attorney, Agent, or Firm* — Buchanan Ingersoll & Rooney PC

(57) ABSTRACT

The present disclosure relates to a process and a production unit that are used to catalytically manufacture olefin trimers from olefin monomers, and wherein olefin dimers are recycled after dimerization reaction, and reacted with olefin monomers in an addition reaction.

19 Claims, 3 Drawing Sheets

OLEFIN TRIMERIZATION

TECHNICAL FIELD

The present disclosure relates to processing of olefins, in particular to producing olefin trimers from olefin monomers with high selectivity.

BACKGROUND

Current methods that are used for polymerizing olefins typically produce a mixture of olefin polymers and the selectivity towards a certain polymer is poor. Production of a desired polymer species from such polymer mixtures requires using complex separation techniques. It would therefore be beneficial to find a process which produces a desired olefin polymer with high selectivity instead of a mixture of polymers, and wherein the olefin monomers are effectively converted into the desired polymers.

U.S. Pat. No. 4,544,791 discloses a two-reactor process which produces 75% dimers and 15% trimers from C4 monomers.

Isododecenes are trimers of isobutene that can be produced by isobutene oligomerization reaction. These trimers have previously been produced in small amounts as unwanted side products in isooctene process, but in isooctene production their amount is usually suppressed by using an oxygen containing moderator substance. However, because olefin trimers can be considered as an interesting product as such, challenge arises how to direct isobutene selectivity dominantly towards trimers without needing to generate and separate either isooctenes (dimers) or heavier oligomers (tetramers and higher polymers).

Acid-catalyzed isobutene oligomerization generally generates a broad oligomer distribution as a function of increasing isobutene conversion. Therefore, previous processes have not been efficient in producing isobutene trimers, i.e. isododecenes. This disclosure relates to a process that achieves a high olefin conversion, and at the same time rich trimer product even to a selectivity of over 90%.

An object of the present disclosure is thus to provide products, processes and systems to alleviate disadvantages discussed above. In particular the present disclosure aims at providing a process and a production unit which can be used to manufacture olefin trimers from olefin monomers with high selectivity.

SUMMARY

The scope of protection sought for various embodiments of the invention is set out by the appended claims.

Herein is disclosed a process for manufacturing olefin trimers comprising:
feeding into a reactor containing a dimerization catalyst:
  olefin monomer feed and at least one oxygen-containing moderator;
operating the reactor at a temperature selected from the range 40-140° C. and at a pressure selected from the range 10-40 bar for carrying out catalytic dimerization reactions between olefin monomers and olefin monomers, and addition reactions between olefin monomers and olefin dimers;
withdrawing a reactor outlet stream from the reactor; and
distilling the reactor outlet stream to separate at least one lighter product comprising olefin dimers, and a heavier bottom product comprising olefin trimers; wherein
at least a portion of the lighter product is recycled into the reactor for providing a recycle feed,
olefin monomers are fed into the reactor predominantly as a fresh olefin monomer feed,
the amount of the fresh olefin monomer feed and the recycle feed fed into the reactor are controlled such that the mass ratio of olefin monomers to olefin dimers entering the reactor is selected from the range 1:8-1:15,
and wherein the catalytic reactions are carried out at operational conditions wherein the olefins remain in liquid phase.

An advantage of the present process is the selectivity of the polymerization reactions (dimerization and addition reactions) for olefin trimers. Another advantage is that with the present process it is possible to carry out the manufacturing of olefin trimers even in a single reactor system, which simplifies the production process. Because dimers produced in the reactor can be recycled after distillation back to the reactor together with other lighter components, no further separation technique is necessary to remove lighter components such as dimers from the olefin trimer product. Thus, the present process achieves a simultaneous recovery of olefin trimers and recycling of reactive species.

Alternatively, a plurality of reactor vessels can be used instead of a single reactor unit, which allows even more control to optimize the selectivity of the process for trimer production. Use of plurality of reactor vessels is also compatible with the single-step distillation described above. Further, the process is flexible in allowing recovery of olefin dimers and olefin trimers as separate product streams. It is also possible to carry out the present invention with two distillation columns, as will be described later.

Herein is also disclosed a production unit, which is suitable for and configured to carry out the above process comprising:
a. at least one reactor unit configured to receive an acid catalyst;
b. at least one distillation column configured to separate isooctene from isododecene;
c. at least one reactor feed line in fluid connection with the reactor unit or the reactor units, and at least one reservoir for olefin monomers;
d. at least one reactor outlet stream line in fluid connection with the reactor unit or the reactor units, and the distillation column;
e. at least one recycle line in fluid connection with the distillation column and the reactor unit or the reactor units; and
f. a bottom product line in fluid connection with the distillation column and a bottom product reservoir.

BRIEF DESCRIPTION OF THE FIGURES

The invention will be described in greater detail by means of non-limiting preferred embodiments with reference to the accompanying figures.

DETAILED DESCRIPTION

Figure 2:
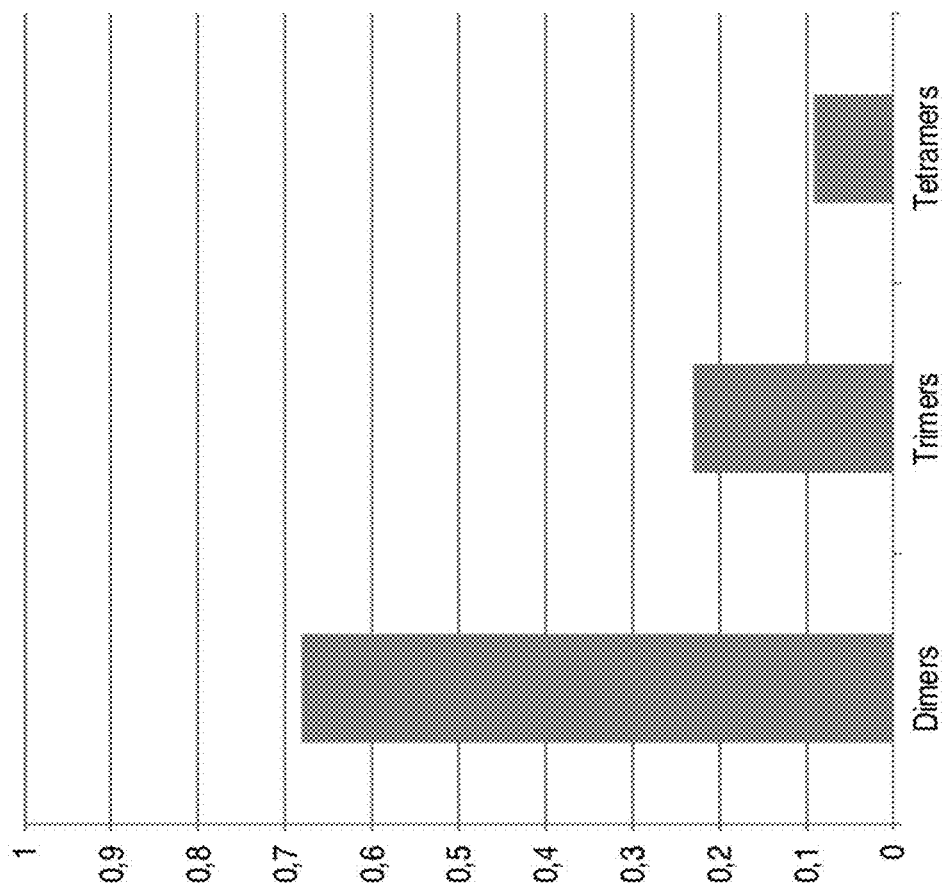
FIG. 2 shows the composition of a comparative bottom product obtained when using "once through" experimental design, i.e. without recycling olefin dimers.

The term oxygen containing moderator refers to a compound which contains oxygen, such as an oxygenate or a compound containing oxygen, carbon and hydrogen.

As used herein, the term "comprising" includes the broader meanings of "including", "containing", and "comprehending", as well as the narrower expressions "consisting of" and "consisting only of".

In an embodiment the process is carried out at an industrial scale, and preferably as a continuous process.

In an embodiment the process steps are carried out in the sequence identified in any aspect, embodiment or claim. In another embodiment any process step specified to be carried out to a product or an intermediate obtained in a preceding process step is carried out directly to said product or intermediate, i.e. without additional, optional or auxiliary processing steps that may chemically or physically alter the product or intermediate between said two consecutive steps.

In the context of the present invention the term reactor feed refers to any feed which enters the reactor. For simplicity, when at least one same component, such as an olefin monomer, is fed into the reactor via multiple feeds, a reactor feed of olefin monomers, or an olefin monomer reactor feed, may in such a cases mean the total feed of said olefin monomers into the reactor.

The terms fresh olefin monomer feed and fresh olefin monomer refer to olefin monomers that are fresh, i.e. non-recycled, and that are fed into the reactor to provide a source of olefin monomers to supplement the amount of olefin monomers that are consumed in the course of catalytic reactions in the reactor, and that are removed from the reactor primarily as a recovered or consumed dimer or trimer product. The fresh olefin monomers are fed in an amount which is sufficient to maintain the mass ratio of monomers to dimers at a desired level. Thus, when the olefin trimer production is running as a continuous process, fresh monomers that have not entered the reactor before are fed into the reactor through the reactor feed line, and olefin trimers are removed from the process as a reaction product.

In an embodiment the olefin monomers are fed into the reactor predominantly as a fresh olefin feed, i.e. the fresh olefin monomers constitute more than 50 wt-% of the total olefin monomers that enter the reactor. In another embodiment at least 55 wt-%, 60 wt-%, 70 wt-%, 80 wt-% or 90 wt-% of the olefin monomers that enter the reactor are fresh.

In an embodiment the recycle feed comprises unreacted olefin monomers.

The term reactor refers to a reactor such as at least one reactor unit, or at least one reactor vessel, wherein the catalytic reactions are carried out. The reactor may comprise at least one catalyst bed and openings for conducting fluids into the reactor and removing fluids from the reactor.

An olefin is a compound composed of at least hydrogen and carbon, and which has at least one double bond between two carbon atoms. Olefins suitable for the present process contain two or more carbon atoms and they may be linear or branched. A preferable olefin monomer in the present invention is isobutene.

An olefin mixture may also be used in the present process and fed into the reactor, such as a mixture of olefin monomers, olefin dimers and heavier polymers, or a mixture containing olefins with varying number of carbon atoms and double bonds. In an embodiment a feed comprising an olefin mixture is fed into the reactor as a mixed feed.

In the context of the present invention the mixed feed or a mixed monomer feed means olefins having different carbon numbers, or a mixture of olefin isomers having the same carbon number, as well as their combination. In an embodiment the mixed feed comprises C4-C5 olefins. In another embodiment the mixed feed comprises olefins having a carbon number C4+/−1. In an embodiment reactive components that are lighter than C4 olefins are removed from the feed entering the reactor to facilitate distillation of the reaction products.

In an embodiment the olefin monomer feed comprises at least one of the following: C4 olefins, C5 olefins, a mixed feed of C4 and C5 olefins, isobutene, 1-butene, cis-2-butene, trans-2-butene; and optionally at least one of inerts, n-butane, i-butane, butadiene, distillation fraction, or any mixture thereof.

In another embodiment the olefin monomer feed, or the mixed feed, comprises or essentially consists of isobutene and at least one of C4 olefins, C5 olefins, a mixed feed of C4 and C5 olefins, 1-butene, cis-2-butene, trans-2-butene, inerts, n-butane, i-butane, butadiene, distillation fraction, or any mixture thereof. In a preferable embodiment isobutene is the major component of the mixed feed.

In an embodiment the amount of non-reactive components such as inerts, n-butane, i-butane in the reactor outlet stream, which exits from the reactor, is so low that they do not significantly hamper separation of olefin dimers and olefin trimers in the distillation step.

An advantage when using a mixed feed in the present process is that removal of inerts present in mixed feeds is effective, and the removal of inerts does not have a significant effect on the product yield. When mixed feeds are used in the present process, very little reactive monomer is left in the reactor outlet stream which exits the reactor, because of the high monomer conversion per pass, and consequently very little monomer is lost in the inert removal step.

The reactor outlet stream, which is withdrawn from the reactor, contains at least olefin dimers and olefin trimers, and optionally smaller amounts of olefin monomers, moderator and inerts.

Figure 3:
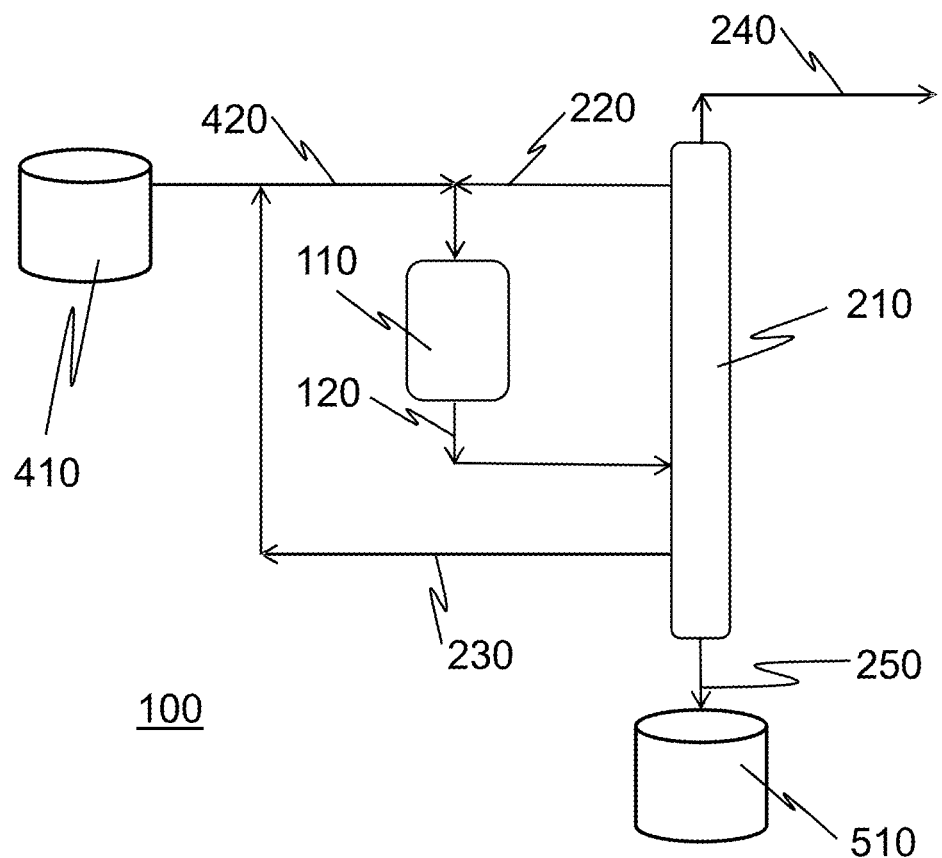
FIG. 3 shows an embodiment of the production unit 100.

An embodiment of a production unit 100 for carrying out the present process is illustrated in FIG. 3. The production unit 100 comprises a reactor unit 110 and a distillation column 210. Olefin monomers are fed into the reactor from a reservoir 410 through a reactor feed line 420, which in FIG. 3 is in fluid communication with a first recycle feed 220, and with a second recycle feed 230. From the reactor unit 110 the reaction products are transferred to the distillation column 210 through a reactor outlet stream line 120. From the distillation column 210 a first recycle line 220 transfers lighter products comprising at least one of olefin monomer, diluent and moderator, back to the reactor unit 110. A second recycle line 230 transfers a stream predominantly composed of olefin dimers back to the reactor unit 110. A heavier bottom product comprising olefin trimers is conducted from the distillation column through a bottom product line 250 to a bottom product reservoir 510. Inerts can optionally be removed through an inerts removal line 240.

In the FIG. 3 embodiment the recycle feed is composed of two recycle feeds conducted through the first recycle line 220 and the second recycle line 230 to the reactor unit 110. In the FIG. 3 the recycle lines are drawn as being fluidly connected to the reactor feed line 420 which enters the reactor unit 110. Alternatively, the recycle lines can be connected to the reactor unit 110 via separate openings in the reactor unit 110.

Instead of two recycle lines 220, 230 described above, a single recycle feed line can also be used. In this embodiment the single recycle line recycles both olefin dimers and olefin monomers, and optionally moderator, back to the reactor.

In an embodiment the olefin monomer reservoir 410 is configured to provide a mixed feed.

In another embodiment the olefin monomer reservoir 410 is configured to provide a fluid communication to a plurality of reactor units, or reactor vessels. In case a plurality of reactor vessels are provided in a series, preferably the olefin monomers are fed to the first reactor vessel of a series, and optionally the latter reactor vessels only receive the feed from the reactor outlet stream line from a previous reactor vessel.

Figure 4:
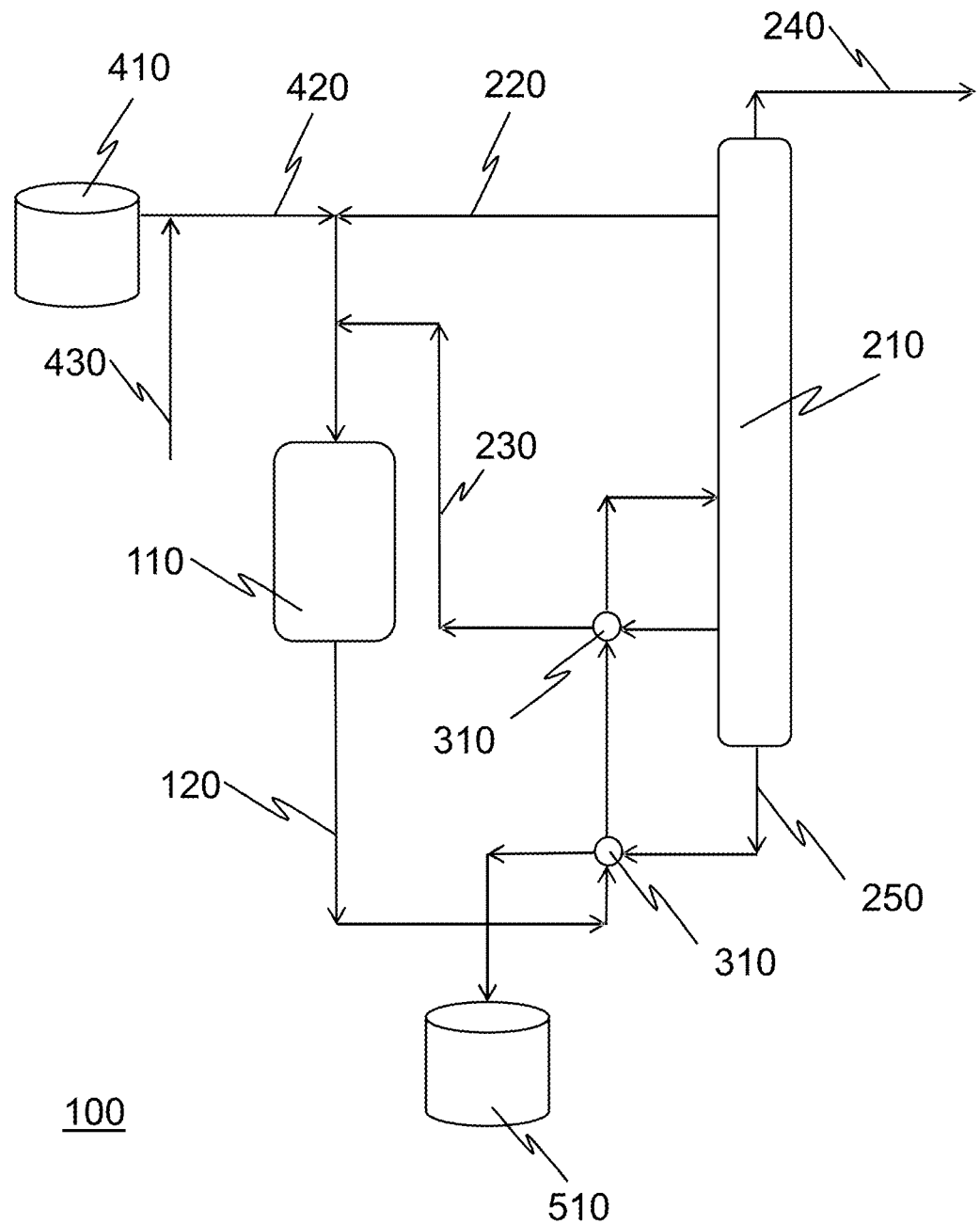
FIG. 4 shows another embodiment of the production unit 100.

Another embodiment of the production unit 100 is illustrated in FIG. 4, in which a mixed feed is preferably used. In this embodiment the production unit 100 comprises a reactor unit 110 and a distillation column 210. Fresh olefins are fed into the reactor from a reservoir 410 through a reactor feed line 420, which in FIG. 4 is in fluid communication with the first a recycle feed line 220, with a second recycle feed 230, and with an optional dimer feed line 430. From the reactor unit 110 the reaction products are transferred to the distillation column 210 through a reactor outlet stream line 120. From the distillation column 210 a first recycle line 220 transfers lighter products comprising at least one of olefin monomer, diluent and moderator, back to the reactor unit 110. A second recycle line 230 transfers a stream predominantly composed of olefin dimers back to the reactor unit 110. A heavier bottom product comprising olefin trimers is conducted from the distillation column through a bottom product line 250 to a bottom product reservoir 510. Inerts can optionally be removed through an inerts removal line 240. FIG. 4 also shows optional heat exchangers 310 that can be used to recover heat from the outlet streams exiting the distillation column, and to heat the reactor outlet stream line 120 before it enters the distillation column. In FIG. 4 olefin dimers are removed from the distillation column through the second recycle line 230 which is fluidly connected to a side of the distillation column to provide a side stream. Preferably the side stream is taken from the distillation column as a vapor outlet stream, which is condensed after heat recovery in the heat exchanger and before entering the reactor unit 110 as a recycle feed.

As shown in FIG. 4, the bottom product line 250 can be conducted through an optional heat exchanger 310 to heat the reactor outlet stream line 120 before the stream enters the distillation column.

In an embodiment an olefin monomer feed, preferably a high purity olefin monomer feed, is fed into a reactor unit, which in the embodiments of FIGS. 3 and 4 is a single reaction vessel. Alternatively, a reactor unit comprising a plurality of reactor vessels can be used.

The reactor unit 110 contains a dimerization catalyst, which catalyzes the formation of olefin dimers in a dimerization reaction between two olefin monomers, and the formation of olefin trimers in an addition reaction between olefin monomers and olefin dimers. Additionally, a small amount of heavier olefin oligomers may form. The reaction product is conducted as a reactor outlet stream 120 from the reactor to the distillation column 210, which separates unreacted inerts, olefin monomers and olefin dimers from a heavier bottom product, which contains at least olefin trimers and optionally compounds having a higher boiling point than olefin dimers. An optional heat exchanger 310 may be used to recover heat from the bottom product containing olefin trimers and to use the recovered heat to heat the reactor outlet stream before it enters the distillation column.

In the embodiment of FIGS. 3 and 4 the moderator can be added to the reactor together with the olefin monomer feed through the reactor feed line 420, together with the recycle feed conducted as the recycle line 220, 230 from the distillation column to the reactor unit, or through a separate inlet (not shown) directly to the reactor. It is preferable to feed the moderator together with a reactor feed entering the reactor such as the reactor feed line 420 or the recycle line 220, 230 to ensure good mixing.

In an embodiment fresh monomers are fed into the reactor as a high purity monomer feed. High purity olefins have preferably a purity of at least 95 wt-%. Use of high purity olefins is particularly advantageous in one column systems, because it results into a reaction product feed, which contains only a small amount of components with an overlapping boiling point with olefin dimers or olefin trimers.

After the olefin stream has passed through the reactor unit or reactor units, the resulting reactor outlet stream is directed to a distillation column, which separates unreacted olefins (mainly dimers) as a lighter product from the olefin trimers that are withdrawn as a bottom product. Preferably the lighter product is substantially free from olefin monomers, which indicates a high conversion rate. In an embodiment the process parameters are selected such that the once-through conversion rate of olefin monomers is at least 96%, whereby the lighter product contains mainly dimers and only a minor amount of olefin monomers. As the monomers are completely or nearly completely consumed in the catalytic conversion, the control of the feeds into the reactor is easier as monomers are added in the feed almost exclusively through the fresh olefin monomer feed, and only a small amount of monomers may be present in the recycled dimer feed. If the lighter product contains dissolved gases, they can be separated from the lighter product by methods known in the art.

In an embodiment the lighter product does not contain olefin trimers. Separation of olefin trimers can be controlled by distillation parameters. In the present process olefin trimers are enriched in the bottom product during distillation and they are removed from the process. Consequently, the recycle feed contains olefin dimers while olefin trimers are preferably not present in the recycle feed in any significant amount.

In an embodiment the bottom product contains less than 15 wt-% olefin tetramers and optionally at least 80 wt-% olefin trimers based on the total weight of the bottom product. In an embodiment the bottom product contains less than 12 wt-% olefin tetramers and optionally at least 80 wt-% olefin trimers based on the total weight of the bottom product. Instead of 80 wt-%, the amount of olefin trimers in the bottom product may also be at least 85 wt-% or at least 88 wt-%.

In an embodiment the once-through conversion rate of olefin monomers is at least 60%, at least 70%, at least 80%, at least 90%, at least 95% or at least 96%, and optionally the selectivity for olefin trimer production is at least 85% or at least 90%, expressed as the weight-% of olefin monomers.

In the context of the present invention the term diluent means any inert agent, or an agent which is less reactive than olefins in the present process. Addition of diluent into the reactor thus lowers the concentration of the olefins in the reactor, the rate of the catalytic conversion of olefins in the process can be controlled by selecting an appropriate amount of diluent.

In an embodiment the recycle feed may be withdrawn from a side of the first distillation column as a side recycle stream. In an embodiment this recycle feed comprises both olefin monomers and olefin dimers. In another embodiment the recycle feed comprises olefin dimers. The position of withdrawing the side recycle stream may thus be selected such that dimers are at least partially removed from the distillation column, while the recycle feed does not contain a significant amount of heavier and lighter compounds.

In the embodiment of FIG. 4 the monomer-containing product and the dimer-containing lighter product can be mixed with the fresh olefin stream before entering the reactor. The amount of the recycled feeds and the amount of fresh olefin can be controlled such that the mass ratio of olefin monomers to olefin dimers in the feeds entering the reactor remains at a desired level. The optional dimer feed line 430 can also be used to feed dimers into the reactor, thereby achieving even more control over the process.

The embodiments described herein are suitable for selective trimer production from olefin monomers, and they allow controlling of the olefinic feeds and moderator such that the selectivity of the catalytic reactions promotes formation of olefin trimers.

The moderator is applied to slightly suppress the reaction rates and to ensure prolonged catalyst life. A favorable moderator amount is specific to the targeted main product and can be selected by the skilled person by analyzing the reaction products and the process conditions. For olefin trimer production a favorable amount is considerably less than used in the production of olefin dimers. Moderator can be recycled back into the reactor from the distillation column together with the recycle feed which contains olefin monomers.

Surprisingly, the inventors found that unlike in isooctene production, a separate solvent is not necessary in the present process which is optimized for producing olefin trimers. Thus, in an embodiment the present process is operated without an additional solvent. In an embodiment the olefinic feed which is fed into the reactor comprises isobutene and recycled olefins (mainly isooctenes) recovered after the feed has passed through the reactor. The present process is advantageous because in a preferable embodiment it can be carried out without a diluent. Prior processes designed primarily for olefin dimer production require use of a diluent, which makes the process uneconomical particularly when feeds with high purity and concentration are used. Advantageously, by the high conversion rate of olefin monomers in the present process, removal of inerts does not cause significant loss of unreacted olefin monomers, which improves efficacy of the process, and improves removal of inerts.

Instead of using a single reactor unit, the reactor unit can be sized and distributed into separate vessels. By increasing the number of reactor vessels and reactor beds, the reaction conditions are easier to control, and consequently an almost complete olefin monomer, such as isobutene, once-through conversion can be achieved. Thermal control of adiabatic temperature rise is also easier when a plurality of reactor units is used.

In an embodiment the reactor unit is comprised of a plurality of reaction vessels arranged as a serial reactor or a parallel reactor, or their combination.

In an embodiment the reactor comprises more than one reactor vessel, such as two, three, four or five reactor vessels each having at least one reactor bed. Use of more than one reactor vessel is advantageous because it allows more detailed control of the temperature, and further allows controlling the amount of moderator and catalyst in each separate reactor vessel. Between the reactor vessels the temperature of the feed can be controlled by temperature control units that can cool or heat the feed. In an embodiment the reaction conditions such as temperature and pressure are essentially the same in each reactor vessels.

When multiple reactor vessels are used as a reactor unit instead of a single reactor vessel, each of the reactor vessels contains a dimerization catalyst, preferably an acidic ion exchange resin catalyst. Preferably the same catalyst is used in each reactor vessel. Preferably the amount of catalyst is kept low in the first reactor vessel, and the amount is increased in the subsequent reactor vessels in the downstream direction of the process. By limiting the amount of catalyst in the first reactor vessel(s) e.g. the temperature is easier to control, and the reaction conditions can be maintained in the selected ranges more easily. For example olefins can be kept in liquid phase when a plurality of reactor vessels are used and the olefin stream is cooled between the reactor vessels, and the mass ratio of olefin monomers to olefin dimers is easier to keep at the desired level. Preferably, in addition to the reactor feed into the first reactor vessel, no further olefins are fed into subsequent reactor vessels during the process, i.e. the fed mixture of olefins is not supplemented with further olefins as the mixture flows through the reactor vessels. When a plurality of reactor vessels is used with a single reactor bed in each reactor vessel, the amount of catalyst may increase in the reactor vessels. In a multiple reactor configuration the upstream reactor vessels contain more catalyst than downstream reactor vessels. In an embodiment a multiple reactor configuration comprises 3 or 4 reactor vessels.

In a reactor unit containing a plurality of reactor vessels, the volume of the reactor vessels may increase from the first reactor vessel to the subsequent reactor vessel(s) in the downstream direction. In an embodiment the volume of the first and the second reactor vessels is substantially the same. In another embodiment the volume of the third and fourth reactor vessels is substantially the same. In yet another embodiment the volume of the third and fourth reactor vessels is substantially identical with respect to each other, but their volume is larger than the volume of the first or second reactor vessels, where the first and the second reactor vessels may have substantially identical volume.

In an embodiment the oxygen-containing moderator, or moderator, is an oxygenate, such as demiwater (demineralized water) or tert-butylalcohol (TBA). Alternatively or additionally, the moderator comprises an alcohol formed inside the reactor as a result of a reaction between water and an olefin. Consequently, e.g. 2-butanol may form from isobutene inside the reactor.

After the olefin stream has passed through the reactor unit, the resulting reactor outlet stream is directed to a distillation column, which separates unreacted olefins (mainly isooctenes) and the moderator component as lighter product from the olefin trimers that are withdrawn as a bottom product. Olefin monomer may be present as a minority species in the lighter product which is mainly composed of olefin dimers. As the monomers are nearly completely consumed in the catalytic conversion, the control of the feed composition inside the reactor is easier as monomers are added only through the fresh olefin monomer feed. If the lighter product contains dissolved gases, they can be separated from the lighter product by known methods.

The moderator may circulate in the recycle-reactor loop together with lighter components and is supplemented to keep its amount at a substantially constant level. Moderator is preferably used in an amount which exceeds the amount of possible water present in the fresh olefin feed or in the recycle feed, which could also serve as a source of oxygenates, but which alone is not sufficient in the present invention. The moderator can be fed into the reactor by mixing it with a feed entering the reactor, such as a reactor feed comprising fresh olefin monomers. Alternatively, the moderator can be mixed with the recycled olefin dimer stream before mixing with the fresh olefin monomers. Use of added moderator in the present process is advantageous because it improves selectivity for trimer production.

At least a portion of the olefin dimers separated during distillation can be recycled back into the reactor. Alternatively or additionally, an external source of olefin dimers, preferably isooctene, is fed into the reactor with olefin monomers.

In an embodiment the reactor outlet stream is distilled to separate olefin dimers that are recycled into the reactor.

In an embodiment components that have not reacted in the reactor are separated as a distillate in a distillation column. Distilled components can either be removed from the process or recycled into the reactor.

In an embodiment the present process is a continuous process. Advantageously the present process allows running the process for a long time, even months, without a need to interrupt the process for maintenance. Prior art processes have used laboratory scale batch processes that are not suitable for industrial scale use because of instability issues. In particular when using a plurality of reactor vessels the trimerization process is effectively under control in the present process, and the continuous process can be run for a long time.

The term dimerization catalyst, or catalyst, refers to a catalyst which catalyzes dimerization of olefin monomers into olefin dimers, and an addition reaction between olefin dimers and olefin monomers to provide olefin trimers. In an embodiment in the present process a majority of the feed entering the reactor contains olefin dimers and the amount of olefin monomers is kept rather low. Consequently, the conditions in the reactor are in the present invention selected such that the dimerization catalyst catalyzes a reaction where an olefin dimer formed in the reactor preferably reacts with an olefin monomer, thereby forming an olefin trimer.

In a preferred embodiment the reactor contains a single catalyst. Preferably the reactor does not contain two different catalysts, from which a first catalyst is specific for dimerization reactions between two monomers but which does not catalyze a reaction between a monomer and a dimer, and from which a second catalyst is specific for reactions between a monomer and a dimer but which does not catalyze a dimerization reaction between two monomers. The present process thus provides an advantage in being simpler compared to prior systems using multiple catalysts.

In an embodiment water is not removed from the reactor or from the lighter product obtained from the distillation column.

In an embodiment the catalytic reactions are carried out at operational conditions wherein the olefins remain in liquid phase, and optionally wherein the moderator also remains in liquid phase. Preferably at least the temperature and the pressure of the reactor(s) are selected such that the olefins are in liquid phase in the reactor. An advantage in keeping at least the olefins in liquid phase is that the control of reactors may be easier to achieve than in a process containing gaseous olefins.

In an embodiment fresh olefin monomers are fed into the reactor, and the fresh olefin monomers comprise olefins having four carbon atoms, preferably isobutene.

In an embodiment olefin dimers are recycled into the reactor by mixing the recycle feed with fresh olefin monomers before feeding the combined feed into the reactor. In an embodiment the olefin dimers are mixed with the reactor feed before the combined mixture enters the reactor. Mixing the olefin dimers with the reactor feed is advantageous because it ensures efficient mixing before contact with the first catalyst. Further, potential differences in temperatures of the two feeds can be dissipated.

In an embodiment the recycle feed contains at least 95 wt-% olefin dimers.

In an embodiment the recycle contains less than 5 wt-% olefin trimers, preferably less than 3 wt-%, 2 wt-% or 1 wt-%. Keeping the amount of olefin trimers low in the recycle feed further improves selectivity of the process towards production of olefin trimers and prevents formation of olefin oligomers having more than three monomer units.

In preferable embodiments the mass ratio of olefin monomers to olefin dimers in the reactor feed is at least about 1:50, 1:40, 1:30, 1:20, 1:15, 1:14, 1:13, 1:12, 1:11, 1:10, 1:9, 1:8, 1:7, 1:6, 1:5, 1:4, 1:3, or 1:2. In a more preferable embodiment the mass feed ratio expressed as the mass ratio of olefin monomers to olefin dimers in the feeds entering the reactor is selected from the range 1:8-1:15 or 1:8-1:10. Using an excess of olefin dimers in the amounts specified above directs the catalytic reaction towards formation of olefin trimers without significantly decreasing the conversion rate of monomers.

In an embodiment the selectivity for olefin trimer production is at least about 85%, preferably about 90% expressed as the weight-% based on the olefin monomers. Depending on the process conditions a selectivity of even about 99% can be achieved. A selectivity of at least 85% means that at least 85% of the olefin monomers are used in the catalytic conversion when olefin dimers and olefin trimers are formed.

In an embodiment the once-through conversion rate of olefin monomers is at least 60%, at least 70%, at least 80%, at least 90%, at least 95% or at least 96%, In an embodiment the dimerization catalyst is an acid catalyst, preferably a strongly acidic ion exchange resin catalyst, most preferably macroreticular acid ion exchange resin catalyst.

In an embodiment the catalyst is solid.

In an embodiment the catalyst catalyzes the dimerization reaction of two olefin monomers, and the addition reaction of an olefin monomer and an olefin dimer.

Advantageously, the present process uses a catalyst and a moderator to improve selectivity of the process for trimer formation. Previously it has been assumed that moderators such as t-butanol or alcohols promote only dimer formation, and that presence of water in the reactor leads into formation of alcohols or ethers, thereby inhibiting trimer and oligomer formation. Consequently, polar compounds such as alcohols or ethers have been previously removed from olefin feedstocks before entering the reactor.

In an embodiment the moderator comprises water, demi-water, alcohol, tert-butyl alcohol, or any combination thereof.

In an embodiment the amount of moderator is selected from the range 0.01-0.5 wt-% of the total feed to the reactor, preferably from the range 0.1-0.4 wt-%, more preferably from the range 0.2-0.3 wt-%. The total feed to the reactor comprises all feeds that are fed into the reactor.

In an embodiment the temperature inside the reactor is selected from the range 40-140° C., preferably from the range 50-130° C., more preferably from the range 60-120° C.

In a preferable embodiment the pressure inside the reactor is selected from the range 15-35 bar, more preferably from the range 20-30 bar.

In a preferable embodiment the reactor is operated at 50-130° C. and 15-35 bar, 50-130° C. and 20-30 bar, 60-120° C. and 15-35 bar, or 60-120° C. and 20-30 bar. Preferably the operating conditions of the reactor are selected such that the olefin monomers and olefin dimers are in liquid phase in the reactor. In an embodiment the residence time of the feed passing through the reactor is 0.25-2 1/h expressed as weight hourly space velocity (WHSV), preferably 0.25-0.4 1/h.

Weight hourly space velocity (WHSV) is defined as the weight of fresh feed flowing per unit weight of the dry catalyst per hour.

In an embodiment the distilling is carried out at a pressure selected from the range 1.8-2 bar, and at a $T_{max}$ of 250° C.

In an embodiment the process further comprises recovering heat from at least one feed obtained from the distillation column.

In an embodiment of the process, the recovered heat is used to heat the reactor outlet stream before it enters the distillation column. In another embodiment the heat is used to heat the reactor feed before it enters the reactor.

In an embodiment the distillation column is a non-reactive distillation column which does not contain catalytic material or a reactive zone, and in which the olefins do not significantly react chemically. The non-reactive distillation column is thus differentiated e.g. from reactive distillation columns that have a reactive zone or a catalytic zone which chemically converts feed components, in particular olefin monomers or olefin dimers or olefin trimers.

In an embodiment the distillation is carried out by using two distillation columns in a series. This embodiment may be advantageous in particular when using a mixed feed which has components with boiling points that may be lower than the boiling points of olefin dimers, or which contains inerts that have a boiling point which is lower than that of olefin dimers. Thus, inerts can be effectively removed by using the two distillation column configuration, and their enrichment can be avoided.

When two distillation columns are used, in the first distillation column light inerts are removed, and optionally one of olefin monomer, diluent and moderator are separated and recycled back into the reactor, whereas olefin dimers and optional heavier compounds are removed as an intermediate bottom product and fed into a second distillation column which separates at least one of olefin dimers, diluent and moderator to be recycled back into the reactor, and olefin trimers and optional heavier compounds are recovered as a bottom product. In a two distillation column process olefin dimers can optionally be recovered from a recycle feed from the second distillation column.

In an embodiment the chemical reactions are carried out in a single reactor. In this embodiment the recycled olefin dimers are conducted to the same reactor where the olefin monomers are dimerized by the dimerization catalyst.

The olefin trimers obtained from the distilling column contain olefin polymers that are formed by polymerizing three olefin monomers together. The olefin monomer components forming the trimers may in an embodiment be chemically identical olefin monomers, such a certain type of C4 olefin, like isobutene, or the trimers may contain at least one lighter or heavier olefin monomer component with a different number of carbon atoms, or an olefin monomer having the same number of carbon atoms but variation in the number of double bonds and/or degree of isomerization.

In an embodiment the reactor is not a trickle bed reactor.

In an embodiment the catalytic reactions are carried out in a different unit than where the distilling is carried out. Thus, in one embodiment the reactions are not carried out in a catalytic distillation column.

In an embodiment the distillation column is operated in an environment where dimerization or oligomerization of the olefins does not occur.

In an embodiment the present process is carried out in the absence of added further solvent, and/or added further inert agent. Advantageously with the present process the dimer itself may serve as an agent which controls the rate of chemical conversion. Additionally, moderator can be recycled into the reactor to control the rate of catalytic conversion in the reactor.

An embodiment of the production unit 100 suitable for carrying out the process of the first aspect is provided in FIGS. 3 and 4.

The production unit optionally contains a heat recovery unit, a heat transfer unit and/or a heater unit.

A heater unit may be arranged in the production unit such that it heats at least one of: reactor feed line, reactor outlet stream line before it enters the distillation column, and distillation column reboiler.

When a plurality of reactor vessels is used, a heat recovery unit, or a cooler unit, can be arranged between the reactor vessels. The heat recovered from the feed which moves from one reactor vessel to a next reactor vessel can preferably be used in heater units of the production unit to improve economy of the process.

In an embodiment of the production unit the reactor comprises a plurality of reactor vessels, wherein each downstream reactor unit contains a larger amount of acid catalyst than the preceding upstream reactor vessel.

In an embodiment of the production unit further comprises at least one heat exchange unit configured to recover heat from the bottom product containing olefin trimers and to use it to heat the reactor outlet stream before it enters the first distillation column.

In an embodiment the production further comprises a first recycle line configured to recycle at least one of olefin monomers, diluent, and modifier through a first recycle line into the at least one reactor, and a second recycle line configured to recycle olefin dimers to the at least one reactor unit.

EXAMPLES

The following examples are provided to better illustrate the claimed invention and are not to be interpreted as limiting the scope of the invention, which is determined by the claims. To the extent that specific materials are mentioned, it is merely for purposes of illustration and is not intended to limit the invention. One skilled in the art may develop equivalent means or reactants without exercising inventive capacity and without departing from the scope of the invention. It shall be understood that many variations can be made in the procedures described herein while still remaining within the scope of the present invention.

An example embodiment of the present process was carried out by running the process with Isobutene:Recycle Feed ratio=0.12 and moderator TBA content 0.37 wt-% in total feed to reactor section. There were three reactors in series each with exit temperature of 90° C. Catalyst was acidic ion exchange resin (5.2 mmol acid eq/g).

Figure 1:
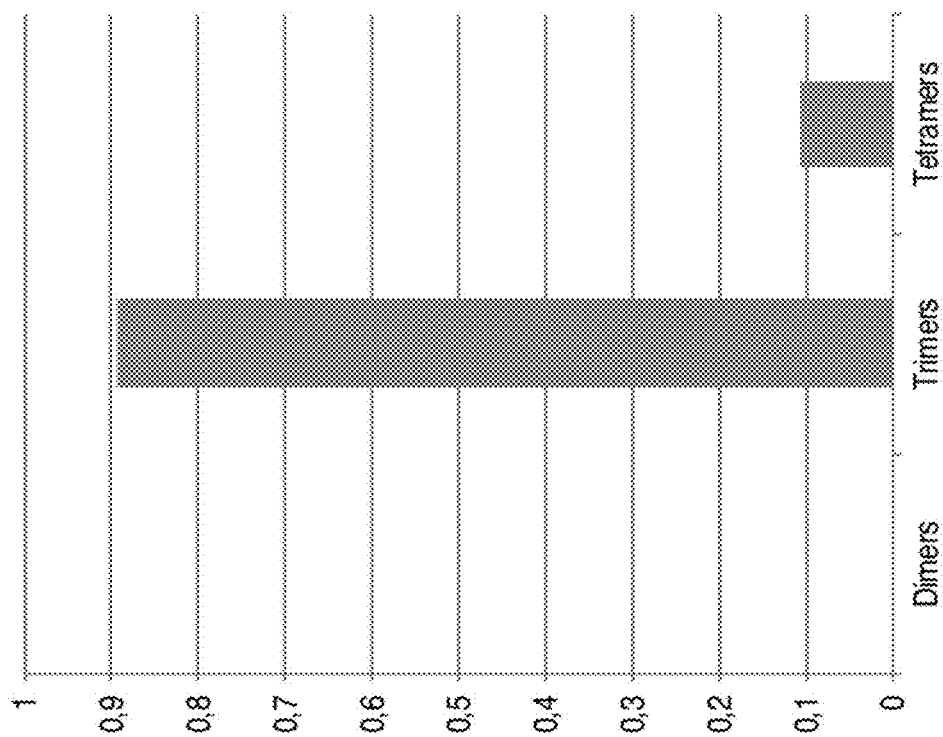
FIG. 1 shows the composition of a bottom product obtained with the preset process with recycled olefin dimers. Nearly 90% conversion of monomers to trimers was achieved.

RESULT: Bottom product composition: 0.0% dimers, 89.2% trimers, 10.8% tetramers, based on the total weight of the bottom product. The results are shown in FIG. 1.

In a comparative example in similar experimental conditions as above the reaction section was run in once through manner with the same isobutene feed and isobutane solvent (50 wt-%) and similar moderator TBA content.

RESULT: Bottom product composition: 68% dimers, 23% trimers, 9% tetramers by weight of the total weight of the bottom product. The analysis results are shown in FIG. 2.

Even-though the dimer content in once-though operation can be further minimized by decreasing the moderator TBA dosage in the feed, at the same time the amount of tetramers will increase and eventually even higher oligomers will appear. Therefore, a substantial trimer selectivity requires both the process configuration with the characteristics described in the present disclosure, and an appropriate dosage of moderator.

Different example embodiments of the present invention have been illustrated in the foregoing. The embodiments are used merely to explain selected aspects or steps that may be utilized when implementing the present invention. Some embodiments may be presented herein only with a reference to a certain aspect of the invention. It should be appreciated that the embodiments may apply to other aspects of the present invention, as well. Consequently, any appropriate combination of the embodiments and the aspects may be formed. Any combination of aspects or embodiments as disclosed herein may also be made without at least one non-essential feature disclosed in an aspect, an embodiment or an example.

The invention claimed is:

1. A process for manufacturing olefin trimers comprising:
   feeding into a reactor containing a dimerization catalyst:
   olefin monomer feed and at least one oxygen-containing moderator;
   operating the reactor at a temperature selected from a range of 40-140° C. and at a pressure selected from a range of 10-40 bar for carrying out catalytic dimerization reactions between olefin monomers and olefin monomers, and addition reactions between olefin monomers and olefin dimers;
   withdrawing a reactor outlet stream from the reactor; and
   distilling the reactor outlet stream to separate at least one lighter product containing olefin dimers, and a heavier bottom product containing olefin trimers; wherein
   at least a portion of the at least one lighter product is recycled into the reactor for providing a recycle feed,
   olefin monomers are fed into the reactor predominantly as a fresh olefin monomer feed,
   amounts of the fresh olefin monomer feed and the recycle feed fed into the reactor are controlled such that a mass ratio of olefin monomers to olefin dimers entering the reactor is selected from a range of 1:8-1:15,
   and wherein catalytic reactions of the reactor are carried out at operational conditions wherein olefins remain in liquid phase.

2. The process of claim 1, wherein the fresh olefin monomers fed into the reactor comprise:
   olefins having four carbon atoms, and/or isobutene.

3. The process of claim 1, wherein the olefin monomer feed comprises:
   at least one of the following: C4 olefins, C5 olefins, a mixed feed of C4 and C5 olefins, isobutene, 1-butene, cis-2-butene, trans-2-butene; and optionally inerts, n-butane, i-butane, butadiene, distillation fraction, or any mixture thereof.

4. The process of claim 1, wherein olefin dimers are recycled into the reactor by mixing the recycle feed with fresh olefin monomers as a combined feed that is fed into the reactor.

5. The method of claim 1, wherein the mass ratio of olefin monomers to olefin dimers is selected from a range 1:8-1:10.

6. The process of claim 1, wherein a selectivity for olefin trimer production is selected to be one or more of at least 85%, and/or at least 90%, expressed as a weight-% based on the olefin monomers.

7. The process of claim 1, wherein a once-through conversion rate of olefin monomers is selected to be one or more of at least 60%, at least 70%, at least 80%, at least 90%, at least 95% and/or at least 96%.

8. The process of claim 1, wherein the dimerization catalyst is selected to be one or more of an acid catalyst, an acidic ion exchange resin catalyst, and/or a macroreticular acid ion exchange resin catalyst.

9. The process of claim 1, wherein the oxygen-containing moderator contains water, demiwater, alcohol, tert-butyl alcohol, or any combination thereof.

10. The process of claim 9, wherein an amount of the oxygen-containing moderator is selected from one or more of a range 0.01-0.5 wt-% of total feed to the reactor, a range 0.1-0.4 wt-% of total feed to the reactor, and/or from a range 0.2-0.3 wt-% of total feed to the reactor.

11. The process of claim 1, wherein an operating temperature of the reactor is selected from one or more of a range 50-130° C., and/or a range 60-120° C.

12. The process of claim 1, wherein an operating pressure of the reactor is selected from one or more of a range 15-35 bar, and/or from a range 20-30 bar.

13. The process of claim 1, wherein a residence time of feed passing through the reactor is one or more of a 0.25-2 1/h expressed as weight hourly space velocity (WHSV), and/or 0.25-0.4 1/h.

14. The process of claim 1, wherein the distilling is carried out at a pressure selected from a range of 1.8-2 bar, and at a $T_{max}$ of 250° C.

15. The process of claim 1, wherein the recycle feed contains at least 95 wt-% olefin dimers.

16. A production unit configured for manufacturing olefin trimers, the production unit comprising:
   a. at least one reactor unit configured to receive an acid catalyst;
   b. at least one distillation column configured to separate isooctene from isododecene;
   c. at least one reactor feed line in fluid connection with the reactor unit and a reservoir for olefin monomers;
   d. at least one reactor outlet stream line in fluid connection with the reactor unit and the distillation column;
   e. at least one recycle line in fluid connection with the at least one distillation column and the at least one reactor unit; and
   f. a bottom product line in fluid connection with the at least one distillation column and a bottom product reservoir;

wherein the production unit comprises:
- a first recycle line configured to recycle at least one of olefin monomers, diluent, and modifier through a first recycle line into the at least one reactor unit; and
- a second recycle line configured to recycle olefin dimers to the at least one reactor unit.

17. The production unit of claim 16, wherein the reactor unit comprises:
- a plurality of reactor vessels, and wherein each reactor vessel downstream of a preceding upstream reactor vessel contains a larger amount of acid catalyst than a preceding upstream reactor vessel.

18. The production unit of claim 17, comprising:
- at least one heat exchange unit configured to recover heat from at least one line from the at least one distillation column.

19. The process of claim 2, wherein the olefin monomer feed comprises:
- at least one of the following: C4 olefins, C5 olefins, a mixed feed of C4 and C5 olefins, isobutene, 1-butene, cis-2-butene, trans-2-butene; and optionally inerts, n-butane, i-butane, butadiene, distillation fraction, or any mixture thereof.

* * * * *